United States Patent [19]

Perchonock

[11] Patent Number: 4,623,535

[45] Date of Patent: Nov. 18, 1986

[54] LEUKOTRIENE ANTAGONISTS

[75] Inventor: Carl D. Perchonock, Philadelphia, Pa.

[73] Assignee: SmithKline Beckman Corporation, Philadelphia, Pa.

[21] Appl. No.: 572,022

[22] Filed: Jan. 19, 1984

[51] Int. Cl.⁴ .................. C07C 149/20; A61K 31/19; A61K 31/205

[52] U.S. Cl. ................. 424/43; 260/501.21; 424/44; 424/45; 514/554; 514/574; 514/826; 514/958; 562/594

[58] Field of Search ............... 562/594; 424/317, 316, 424/43, 45, 44; 260/501.21; 514/574, 554, 826

[56] References Cited

U.S. PATENT DOCUMENTS 2,602,816  7/1952  Gregory et al. ............. 562/594
3,217,004  10/1965  Hechenbleikner et al. ..... 260/429.7
3,742,031  6/1973  Lafon ..................... 562/594

FOREIGN PATENT DOCUMENTS 1087089  10/1967  United Kingdom .............. 562/594

OTHER PUBLICATIONS

Yasuo Kishimoto et al, Yakugaku Zasshi, 73:447–50 (1958).
Kogo et al, Chemical Abstracts, 89:130417q (1978).

Primary Examiner—Vivian Garner
Attorney, Agent, or Firm—Richard D. Foggio; Stuart D. Suter; Alan D. Lourie

[57] ABSTRACT

The compounds represented by the following structural formula (I)

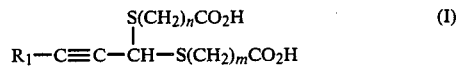

wherein m and n are independently 1, 2 or 3; $R_1$ is an $C_8$ to $C_{13}$ alkyl radical and pharmaceutically acceptable salts thereof have been found to be leukotriene antagonists and useful in the treatment of diseases in which leukotrienes are a factor, such as asthma.

14 Claims, No Drawings

LEUKOTRIENE ANTAGONISTS

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$ ($LTD_4$) and leukotriene-$E_4$ ($LTE_4$), the structural formulae of which are represented below.

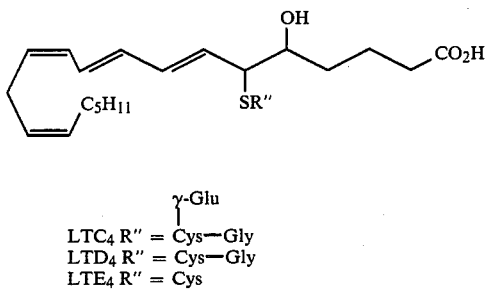

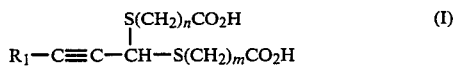

$LTC_4$ R" = Cys—Gly
$LTD_4$ R" = Cys—Gly
$LTE_4$ R" = Cys

By antagonizing the effects of $LTC_4$, $LTD_4$ and $LTE_4$ or other pharmacologically active mediators at the end organ, airway smooth muscle, the compounds and pharmaceutical compositions of the instant invention are valuable in the treatment of diseases in which leukotrienes are a factor, such as asthma.

DETAILED DESCRIPTION OF THE INVENTION

The compounds of this invention are represented by the following general structural formula (I)

wherein m and n are independently 1, 2 or 3 and $R_1$ is a $C_8$ to $C_{13}$ alkyl radical and the pharmaceutically acceptable salts thereof.

Particular compounds of this invention are those compounds of the formula (I) wherein both m and n are two. These compounds, which are designated 4,6-dithianonanedioic acid derivatives, are exemplified by 4,6-dithia-5-(1-tetradecynyl)-nonanedioic acid; 4,6-dithia-5-(1-dodecynyl)-nonanedioic acid and 4,6-dithia-5-(1-decynyl)-nonanedioic acid.

The compounds of this invention also include those compounds of the formula (I) wherein both m and n are three. These compounds, which are designated 5,7-dithiaundecanedioic acid derivatives, are exemplified by 5,7-dithia-6-(1-dodecynyl)-undecanedioic acid.

Additional compounds of this invention are those compounds of the formula (I) wherein both m and n are one. The compounds which are designated 3,5-dithiaheptanedioic acid derivatives are exemplified by 3,5-dithia-4-(1-dodecynyl)-heptanedioic acid.

Further illustrations of the compounds of this invention are the 3,5-dithiaoctanedioic acid derivatives where m is 1 and n is 2, and the 4,6-dithiadecanedioic acid derivatives where m is 2 and n is 3.

The compounds of the formula (I) are acidic and are, therefore, capable of forming salts with pharmaceutically acceptable bases according to procedures well known in the art. Such acceptable bases include organic and inorganic bases, such as ammonia, organic amines, and alkali metal bases.

The compounds of the formula (I) are conveniently prepared by forming the dithioacetal derivatives from the acetals of the following structural formula (II)

$$R_1C\equiv CCH(OR_2)_2 \qquad (II)$$

wherein $R_1$ is described above and $R_2$ is an alkyl radical of one to four carbon atoms or both $R_2$'s taken together form an alkylene radical of two to three carbon atoms, utilizing the appropriate mercaptoalkanoic acid. The reaction of the acetal of the formula (II) with two equivalents of mercaptoalkanoic acid is accomplished at low to moderate temperatures under acidic conditions in an inert solvent or excess mercaptoalkanoic acid. Examples of such inert solvents included chlorinated hydrocarbons, such as methylene chloride, chloroform and dichloroethane. The acidic conditions are produced by mineral acids, such as hydrochloric acid and sulfuric acid or Lewis acids, such as boron trifluoride etherate. The reaction temperatures can range from −40° C. to ambient temperatures.

The leukotriene antagonist activity of the compounds of this invention is measured by the ability of the compounds to inhibit the leukotriene induced contraction of guinea pig tracheal tissues in vitro. The following methodology was employed:

In vitro: Guinea pig (adult male albino Hartley strain) tracheal spiral strips of approximate dimensions 2 to 3 mm cross-sectional with and 3.5 cm length were bathed in modified Krebs buffer in jacketed 10 ml tissue bath and continuously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1 μM) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the contractions elicited by $LTD_4$ were standardized as a percentage of the maximum response obtained to a reference agonist, carbachol (10 μM).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The $-\log K_B$ value for the test compound was determined by the following equations:

$$\frac{EC_{30} \text{ (presence of test compound)}}{EC_{30} \text{ (presence of vehicle control)}} = \text{dose ratio} = X \quad 1$$

$$K_B = \text{concentration of test compound}/(X - 1) \quad 2$$

The compounds of this invention possess biosignificant antagonist activity against leukotrienes, primarily leukotriene $D_4$. The antagonist activity of representative compounds of this invention is tabulated below. The $-\log K_B$ values were calculated from the above test protocol.

| Compounds of the Formula (I) | | | In Vitro |
| --- | --- | --- | --- |
| $R_1$ | m | n | $-\log K_B$ |
| $C_{12}H_{25}$ | 2 | 2 | 5.7 |
| $C_{10}H_{21}$ | 2 | 2 | 6.1 |
| $C_8H_{17}$ | 2 | 2 | 5.0 |
| $C_{10}H_{21}$ | 3 | 3 | 5.5 |
| $C_{10}H_{21}$ | 1 | 1 | 5.3 |

The specificity of the antagonist activity of a number of the compounds of this invention is demonstrated by relatively low levels of antagonism toward agonists such as potassium chloride, carbachol, histamine and $PGF_{2\alpha}$.

Pharmaceutical compositions of the present invention comprise a pharmaceutical carrier or diluent and an amount of a compound of the formula (I) or a pharmaceutically acceptable salt, such as an alkali metal salt thereof sufficient to produce the inhibition of the effects of leukotrienes, such as symptoms of asthma and other allergic diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid paraffins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension.

Usually a compound of formula I is administered to an animal subject in a composition comprising a nontoxic amount sufficient to produce an inhibition of the symptoms of an allergic response. When employed in this manner, the dosage of the composition is selected from the range of from 350 mg to 700 mg of active ingredient for each administration. For convenience, equal doses will be administered 1 to 4 times daily with the daily dosage regimen being selected from about 350 mg to about 2800 mg.

The pharmaceutical preparations thus described are made following the conventional techniques of the pharmaceutical chemist as appropriate to the desired end product.

Included within the scope of this disclosure is the method of inhibiting the symptoms of an allergic response resulting from a mediator release which comprises administering to an animal subject a therapeutically effective amount for producing said inhibition of a compound of formula I, preferably in the form of a pharmaceutical composition. The administration may be carried out in dosage units at suitable intervals or in single doses as needed. Usually this method will be practiced when relief of allergic symptoms is specifically required, however, the method is also usefully carried out as continuous or prophylactic treatment. It is within the skill of the art to determined by routine experimentation the effective dosage to be administered from the dose range set forth above, taking into consideration such factors as the degree of severity of the allergic condition being treated, and so forth.

The following examples illustrate the preparation of the compounds of this invention and their incorporation into pharmaceutical compositions and as such are not to be considered as limiting the invention set forth in the claims appended hereto.

EXAMPLE 1

Preparation of 4,6-Dithia-5-(1-decynyl)-nonanedioic Acid (a) 1,1-dimethoxy-2-undecyne To freshly prepared ethyl magnesium bromide (from 61 mmoles bromoethane and 63 mmoles magnesium) was added 1-decyne (50 mmoles) in diethyl ether (10 ml) dropwise at ambient temperature. The reaction mixture was then heated at reflux for 2 hours. After cooling the reaction mixture, trimethylorthoformate (75 mmoles) in diethyl ether (10 ml) was added and the resultant mixture heated to distill off the diethyl ether. The resultant paste was taken up in anhydrous toluene (50 ml) and heated at reflux for 1 hour. The reaction mixture was poured into saturated ammonium chloride (50 ml) and then extracted with diethyl ether ($3 \times 50$ ml). The organic phase was washed with water ($3 \times 20$ ml) and dried over anhydrous magnesium sulfate. Evaporation of the organic phase afforded the desired product as an oil.

(b) 4,6-Dithia-5-(1-decynyl)-nonanedioic acid

To an ice cold solution of the compound of Example 1(a) (5 mmoles) and 3-mercaptopropionic acid (11.5 mmoles) in methylene chloride (20 ml) was added dropwise boron trifluoride etherate (5.5 mmoles). After about 15 minutes, the reaction mixture was poured onto ice (10 g) and extracted with diethyl ether (3×20 ml). The organic phase was washed with water (3×20 ml) and dried over anhydrous magnesium sulfate. Evaporation of the organic phase afforded an oil which was purified by flash chromatography over silica gel with hexane:ethyl acetate:formic acid (70:30:0.5) as eluant to yield the desired product as an oil. Treatment of the oil with petroleum ether gave a solid material (mp 63°–65° C.).

Analysis for $C_{17}H_{28}O_4S_2$: Calculated: C, 56.64; H, 7.83. Found: C, 56.81, H, 7.89.

The following compounds were prepared according to the general method described above from the appropriate alkyne and mercaptoalkanoic acid:

4,6-dithia-5-(1-tetradecynyl)-nonanedioic acid mp 60°–63° C.);

4,6-dithia-5-(1-dodecynyl)-nonanedioic acid (mp 59°–61° C.);

5,7-dithia-6-(1-dodecynyl)-undecanedioic acid (mp 56°–57° C.); and 3,5-dithia-4-(1-dodecynyl)-heptanedioic acid (mp 64°–65° C.).

Similarly, the following compounds of the formula (I) are prepared utilizing the general method of Example 1 from the appropriate reactants:

| m | n | $R_1$ |
|---|---|---|
| 1 | 2 | $C_{12}H_{25}$ |
| 1 | 1 | $C_8H_{17}$ |
| 2 | 3 | $C_{12}H_{25}$ |
| 3 | 3 | $C_8H_{17}$ |

EXAMPLE 2

As a specific embodiment of a composition of this invention, an active ingredient, such as the compound of Example 1(b), is dissolved in 25 mM sodium carbonate at a concentration of 0.4 percent and aerosolized from a nebulizer operating at an air flow adjusted to deliver the desired aerosolized weight of drug.

EXAMPLE 3

As an additional specific embodiment of a composition of this invention, an active ingredient, such as the compound of Example 1(b), is admixed with mannitol at a concentration of 1.0 percent and administered from a powder inhalation device adjusted to deliver the desired weight of drug.

What is claimed is:

1. A compound represented by the following structural formula (I):

$$R_1-C\equiv C-\underset{\displaystyle S(CH_2)_nCO_2H}{\overset{|}{C}H}-S(CH_2)_mCO_2H \quad (I)$$

wherein m and n are independently 1, 2 or 3 and $R_1$ is an alkyl radical containing 8 to 13 carbon atoms or a pharmaceutically acceptable salt thereof formed with ammonia, an organic amine or an alkali metal base.

2. A compound of claim 1 wherein both m and n are two or a pharmaceutically acceptable salt thereof formed with ammonia, an organic amine or an alkali metal base.

3. A compound of claim 2 which is 4,6-dithia-5-(1-tetradecynyl)-nonanedioic acid.

4. A compound of claim 2 which is 4,6-dithia-5-(1-dodecynyl)-nonanedioic acid.

5. A compound of claim 2 which is 4,6-dithia-5-(1-decynyl)-nonanedioic acid.

6. A compound of claim 1 wherein both m and n are three or a pharmaceutically acceptable salt thereof formed with ammonia, an organic amine or an alkali metal base.

7. A compound of claim 6 which is 5,7-dithia-6-(1-dodecynyl)-undecanedioic acid.

8. A compound of claim 1 wherein both m and n are one or a pharmaceutically acceptable salt thereof formed with ammonia, an organic amine or an alkali metal base.

9. A compound of claim 8 which is 3,5-dithia-4-(1-dodecynyl)-heptanedioic acid.

10. A pharmaceutical composition for inhibiting the symptoms of asthma in subjects in need of such inhibition comprising a pharmaceutical carrier or diluent and a nontoxic amount sufficient to produce said inhibition of a compound of claim 1.

11. A pharmaceutical composition according to claim 10 in a form suitable for administration by inhalation.

12. A pharmaceutical composition according to claim 11 in the form of an aersol formulation.

13. A pharmaceutical composition according to claim 10 in a form suitable for administration by parenteral adminstration.

14. A pharmaceutical composition according to claim 13 in the form of a sterile solution.

* * * * *

Notice of Adverse Decision in Interference

In Interference No. 102,234, involving Patent No. 4,623,535, C. D. Perchonock, LEUKOTRIENE ANTAGONISTS, final judgment to the patentee was rendered Mar. 20, 1990, as to claims 1-14.
(*Official Gazette May 8, 1990*)